United States Patent
Jose

[11] Patent Number: 6,153,805
[45] Date of Patent: Nov. 28, 2000

[54] PROCESS FOR OBTAINING CYCLOHEXANE BY CATALYTIC BENZENE HYDROGENATION

[75] Inventor: Anibal Miguel Jose, La Plata, Argentina

[73] Assignee: YPF S.A., Buenos Aires, Argentina

[21] Appl. No.: 09/335,896

[22] Filed: Jun. 18, 1999

[30] Foreign Application Priority Data

Jun. 19, 1998 [AR] Argentina ............... P 98 01 02945

[51] Int. Cl.$^7$ .................. C10C 5/10; C10G 45/44
[52] U.S. Cl. ............. 585/269; 585/266; 585/270; 208/145
[58] Field of Search ............. 208/145; 585/266, 585/269, 270

[56] References Cited

U.S. PATENT DOCUMENTS 4,153,637  5/1979  De Vleessschauwer et al. ...... 585/405
4,731,496  3/1988  Hu et al. .................................. 585/270

*Primary Examiner*—Bekir L. Yildirim
*Attorney, Agent, or Firm*—Birch, Stewart, Kolasch & Birch, LLP

[57] ABSTRACT

A process for the obtention of low impurity cyclohexane content, practically methylcyclopentane (MCP) free, by catalytic hydrogenation of benzene in gas phase in the presence of group VIII metal catalyzers. The catalytic hydrogenation is performed in the presence of ammonia or nitrogenated organic basis as MCP formation inhibitors, being incorporated in a 0.2 to 100 ppm concentration.

4 Claims, 1 Drawing Sheet

PROCESS FOR OBTAINING CYCLOHEXANE BY CATALYTIC BENZENE HYDROGENATION

SUMMARY OF THE INVENTION

The present invention is related to catalytic hydrogenation of benzene. More specifically, the invention refers to an improved process for obtaining low impurity content cyclohexane, almost methylcyclopentane free (MCP), being benzene catalytically hydrogenated in gas phase, in the presence of nitrogenated basis as MCP and other contaminant formation inhibitors. Said invention potentiates the use of hydrogenation in gas phase, practically obsolete without the improvement proposed herein, thus placing it at the top of hydrogenation industrial procedures.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

BACKGROUND OF THE INVENTION

Figure 1:
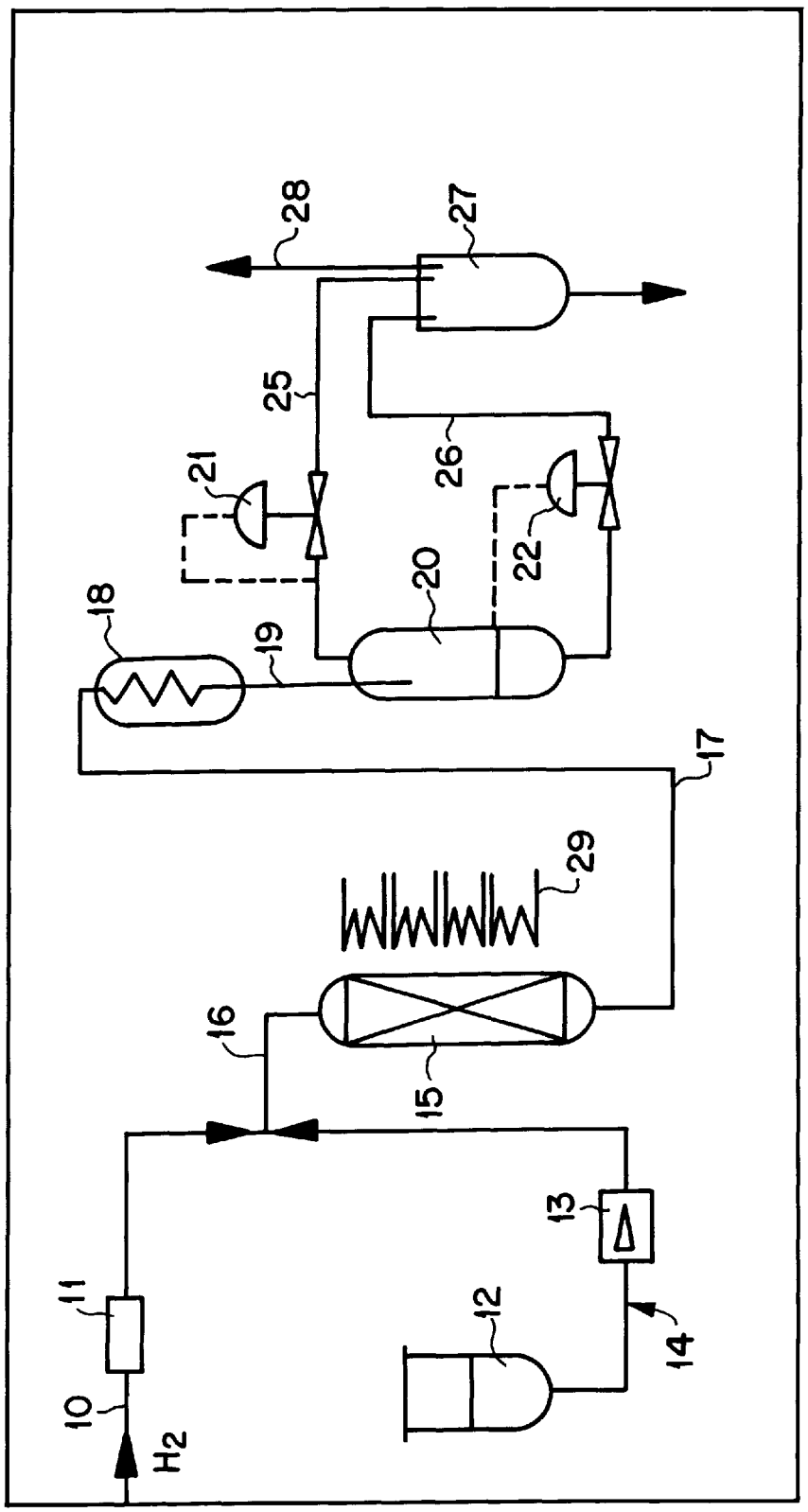
FIG. 1 shows an example of putting the present invention into practice.

It is well known that cyclohexane is a widely applied hydrocarbon in the industry, essentially when obtaining caprolactam, which is an intermediary in the manufacturing of nylon 6.

Industrial cyclohexane obtention is mostly due to catalytic hydrogenation of benzene, either through liquid phase hydrogenation, catalyzed, for example, with Ni Raney at 150° C. and about 15 atmosphere pressures (Sabatier, Ind. Eng. Chem. 18, 1005 (1925)) or through the process developed by the Institut Francais du Petrole wherein benzene and hydrogen-rich gas is fed to a liquid-phase reactor containing Raney nickel catalyst. The nickel suspension is circulated to improve heat removal, the benzene being completely hydrogenated in a second fixed-bed reactor. Said catalytic hydrogenation of benzene can also be carried out by hydrogenation in gas phase, catalyzed with noble metals, mainly platinum supported over alumina, etc., at 200° C. temperatures and about 30 kg/cm2 pressures. Benzene production technologies enable the obtention of high purity benzene, being its purity degree of over 99.99%. Hence, cyclohexane that is thus obtained by hydrogenation could have similar purity levels. However, hydrogenation reactions take place along with secondary reactions that produce undesired contaminants especially methylcyclopentane (MCP).

It has been considered that benzene conversion (g) to cyclohexane follows the following scheme:

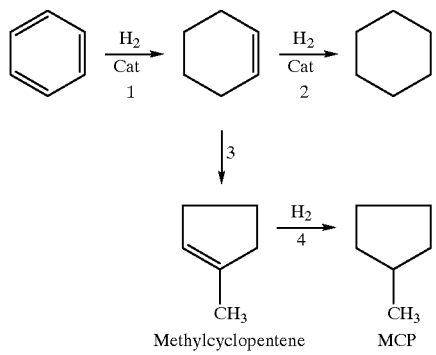

The development of the secondary reaction (3) may be explained as being a result of the combination of two adverse factors:
i) destabilization (or labilization) of C—H bonds, ascribed to platinum, and
ii) weakening of C—C bond energy, ascribed to dynamic accumulation of electrons in certain points of the catalyst, that would function as "acid" zones (electron emitting), thus favoring isomerization of cyclohexane (step 3).

Said effects are increased when reaction temperature increases, thus generating over 150 ppm MCP when working at over 300° C. temperatures.

Normally, temperature peaks that exceed said value occur due to exothermicity of the process.

The aim of having high purity cyclohexane that meets determined specifications has generated several attempts to try to reduce temperature at reaction zone, diluting the catalyst bed with inert materials. Particularly in the frontal zone of the catalytic bed, wherein reaction speed is higher due to higher benzene concentration (or activity), also temperature is higher.

When diluting catalyst "concentration" in the frontal zone (or entrance zone) of the catalytic bed, it is possible, thus, to maintain the temperature of that zone below limits compatible with tolerated MCP contents, but at the expense of larger equipment (due to the fact that there are larger catalytic zones).

However, if catalytic zones are not re-measured, the same result could be achieved through lower global conversion speeds.

In other words, any attempt to reduce MCP amount lowering reaction temperature shall lead to a dramatic reduction in production capacity of a given system.

This difficulty is also accompanied by the fact that it is not easy to keep temperature between certain limits, which in turn makes the control of this type of units more difficult.

The above mentioned solutions have not led to the obtention of highly satisfactory results, mainly with reference to the obtention of cyclohexane according to current specifications, more severe for MCP limit values allowed.

Some improvement has been achieved using nickel instead of platinum catalysts, thus meeting quality requirements although not being able to take full advantage of caloric energy generated by the process due to the need to work at relatively low temperatures. Here, there is also relatively lower reaction speed compared to hydrogenation at higher temperatures, thus, involving larger equipment, less efficiency of the catalyst, etc. U.S. Pat. No. 4,731,496, to Shao-Chuch Hu et al. describes the conversion of benzene into cyclohexane by a gas-phase hydrogenation over a specific supported nickel catalyst located on a fixed bed reactor, wherein mixed Ti—Zr metal oxides in place of conventional alumina or diatomaceous earth are used as the supports.

Another popular technology consists of hydrogenation in liquid phase, with a catalyst that is continually added to the feeding source.

Although a good quality cyclohexane is achieved in this way, the inconvenience of a continuous consumption of catalyst is added to the generation of residues (exhausted catalyst) that forces to a later disposition of said catalyst as dangerous residue.

However, the most serious disadvantage of this technology lies in the fact that low reaction temperature prevents the full exploitation of the enormous amount of caloric energy generated by hydrogenation, which in gas phase process is totally recoverable.

It has now been seen that it is possible to insist on platinum as benzene hydrogenation catalyst, considering all the advantages offered by this catalytic agent (which would allow the redesigning of proper facilities), namely: temperatures and high reaction speeds and without claimed disadvantages: pollution of cyclohexane-product with MCP in high undesired concentrations, above current specifications.

In practice and considering the experiences indicated below, this implies benzene conversion shall be carried out under "sui generis" conditions determined by the presence of nitrogenated, inorganic bases such as ammonia or organic bases such as pyridine, alkylamine in the hydrogenation zone, fed either with hydrogen or with benzene load or injected directly to the reaction zone.

BRIEF SUMMARY OF THE INVENTION

The main aim of the present invention is an improved process to obtain cyclohexane by catalytic hydrogenation of benzene in gas phase and in presence of group VIII metal catalysts, characterized in that said catalytic hydrogenation is performed in the presence of ammonia or nitrogenated organic bases, as methylcyclopentane formation inhibitors, incorporated to said gas phase in a 0.2 to 100 ppm concentration, followed by the separation of effluent from the catalytic hydrogenation zone, by adsorption of inhibitors used in said zone and degrading products and thus recover formed cyclohexane.

The process, object of said invention allows for the obtention of high purity cyclohexane that meets strict specifications of international markets. Performed experiences, summarized below, have made it possible to verify the obtention of cyclohexane with maximum impurity levels of 150 ppm and cyclohexane concentrations of about 99.98% with an MCP content that has decreased up to 35 ppm.

Particularly, the advantages of the present invention are applicable in hydrogenation of benzene catalyzed with noble materials, especially platinum. Pt influence in the weakening of C—H energy link—already discussed—seems to be an important enough factor (at high temperatures registered in benzene conversion zones) to promote the development of secondary effects that lead to cyclohexane isomerization and MCP formation.

Even though the following descriptions and experiments are closely related to platinum, it shall be understood that this does not imply a limitation for the ends and purposes of the present invention which is related to other group VIII elements of well known catalytic activity in benzene hydrogenation, such as nickel.

It is considered that secondary reactions that lead to MCP formation and other impurities are catalyzed or co-catalyzed through the formation or presence of zones or "acid" locus in catalytic mass, which would be blocked or inhibited by nitrogenated bases applied according to the principles of the present invention.

Moreover, not all bases work with the same efficiency under the same conditions; it shall be noted that in this aspect, ammonia inhibiting activity has enabled the reduction of MCP concentration in cyclohexane product under 35 ppm; probably said concentration could be reduced even more if desired.

The following example shows a possible way of putting into practice the present invention associated with the installation shown in FIG. 1.

EXAMPLE

In said figure reference 10 refers to H2 (g) feeding from a source (not shown), led through canalization 10 of regulated caudal according to 11. At the same time benzene is held from the source 12, through the pump 13, while ammonia from another source is injected at the pump suction with a dossier (not shown) through the line 14. Benzene with ammonia, already at a 30 kg/cm2, meets with gas hydrogen and enters together with the reactor 15, through a common canalization 16. Said reactor 15 contains the catalytic bed of which no details are shown.

Reference 29 globally refers to heating means associated to the reactor 15, whose function is keep conversion zone temperature within predetermined limits compatible with the kinetic of hydrogenation reaction.

Canalization 17 drives the gas effluent of reactor 15 (cyclohexane+ammonia+contaminants) to a condenser 18, afterwards accessing the high pressure separator 20 through the level control valve 22 while the gas fraction does so through the pressure control valve 21.

Both effluent currents 26 and 25 respectively, access the low pressure separator 27, from which, high purity cyclohexane 30 is obtained from the bottom. Gas fraction leaves the separator 27 through 28 and is then driven to an adsorption tower through a zeolite, clay or alumina where excess ammonia is retained, being then driven to a recovery and purification unit (not shown).

WORKING CONDITIONS

Entrance temperature at the reactor: 200° C.

Maximum temperature at the bed: 400° C.

Pressure: 30 kg/cm2.

Length of each experience: 7 days.

RESULTS:

|  | WITH AMMONIA (2 ppm) | WITHOUT AMMONIA |
|---|---|---|
| MCP in cyclohexane | <100 ppm | >700 ppm |
| Cyclohexane purity | 99.98% | 99.92% |
| Others (methylcyclohexane) | BALANCE | BALANCE |

NOTE: Methylcyclohexane present in the product obviously comes from toluene that accompanies benzene used as reactant and that is hydrogenated in the reaction.

These results show the inhibiting effect of NH3 valued in view of the content of impurities in the recovered cyclohexane as opposed to the product obtained through the conventional technique (without NH3).

The same experiment, repeated with pyridine instead of ammonia, also led to the obtention of cyclohexane with less MCP content.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for obtaining cyclohexane by catalytic hydrogenation of benzene in gas phase in the presence of group VIII metal catalyzers, comprises the steps of said catalytic hydrogenation being carried out in presence of ammonia or nitrogenated organic basis, as methylcyclopentane formation inhibitors, being incorporated in an 0.2 to 100 ppm, optionally separating the inhibitor present in the reaction gas effluent through adsorption by a zeolite, clay or alumina bed, being produced cyclohexane the liquid effluent.

2. The process according to claim 1, wherein inhibitors are incorporated to the liquid benzene feeding phase.

3. The process according to claim 1, wherein the inhibitor is ammonia incorporated in a 2 ppm concentration with reference to fed benzene.

4. The process according to claim 1, wherein organic basis is pyridine.

* * * * *